(12) United States Patent
Langer

(10) Patent No.: US 11,224,534 B2
(45) Date of Patent: Jan. 18, 2022

(54) SCROTAL EDEMA PRESSURE REDISTRIBUTION DEVICE

(71) Applicant: GLOBAL MEDICAL FOAM, INC., Lexington, OH (US)

(72) Inventor: Victoria A. Langer, Lexington, OH (US)

(73) Assignee: GLOBAL MEDICAL FOAM, INC., Lexington, OH (US)

(*) Notice: Subject to any disclaimer, the term of this patent is extended or adjusted under 35 U.S.C. 154(b) by 120 days.

(21) Appl. No.: 16/726,787

(22) Filed: Dec. 24, 2019

(65) Prior Publication Data

US 2020/0206015 A1 Jul. 2, 2020

Related U.S. Application Data

(60) Provisional application No. 62/784,938, filed on Dec. 26, 2018.

(51) Int. Cl.
*A61F 5/40* (2006.01)
*A61F 5/451* (2006.01)

(52) U.S. Cl.
CPC ............. *A61F 5/40* (2013.01); *A61F 5/451* (2013.01)

(58) Field of Classification Search
CPC ....... A61B 9/02; A61B 9/023; A61B 2400/38; A61B 2400/20; A61B 2400/32; A61B 9/001; A61B 9/004; A61B 9/12; A61B 9/026; A61B 9/14; A61B 9/00; A61B 17/00; A61B 2300/32; A61B 2400/44; A61B 2400/52; A61F 5/40; A61F 5/451; A61F 7/08; A61F 6/20; A61F 6/202; A61F 6/204
See application file for complete search history.

(56) References Cited

U.S. PATENT DOCUMENTS

| | | | | |
|---|---|---|---|---|
| 4,615,337 A | * | 10/1986 | Allinson | A61F 5/41 600/39 |
| 7,296,307 B2 | * | 11/2007 | Atwater | A63B 71/12 128/846 |
| 9,393,151 B2 | * | 7/2016 | Gallen | A61F 7/02 |

* cited by examiner

*Primary Examiner* — Ophelia A Hawthorne
(74) *Attorney, Agent, or Firm* — Jacob M. Ward; Ward Law Office LLC

(57) ABSTRACT

A scrotal edema support has a main body with a top surface, a bottom surface, a first side, a second side, a rear end, and a front end. The top surface includes a flexing area and a resting area. The flexing area is disposed adjacent to the rear end of the main body. The resting area is disposed adjacent to the front end of the main body. The flexing area is configured to receive an edematous scrotum of a patient. The bottom surface has a sloped portion and a leveled portion. The sloped portion is disposed adjacent to the rear end of the main body. The leveled portion is disposed from the front end to the sloped portion. The sloped portion of the bottom surface is oriented at an angle relative to the leveled portion of the bottom surface.

19 Claims, 5 Drawing Sheets

SCROTAL EDEMA PRESSURE REDISTRIBUTION DEVICE

CROSS-REFERENCE TO RELATED APPLICATIONS

This application claims the benefit of U.S. Provisional Application No. 62/784,938, filed on Dec. 26, 2018. The entire disclosure of the above application is hereby incorporated herein by reference.

FIELD

The present disclosure relates to a medical support device and, more particularly, to a device for cushioning and supporting a male patient with scrotal swelling or edema.

BACKGROUND

Scrotal swelling, also known as scrotal edema, is a very serious condition and a true medical emergency. The swelling may interrupt blood flow to the testicles and can lead to tissue death of the testicles. Scrotal edema can occur from a plethora of medical conditions, such as a twisted testicle, cancer, kidney failure, and hernias.

Due to the swelling associated with this condition, the scrotum of the patient receives increased pressure. The nervous system of the patient perceives this increased pressure on the scrotum as a risk of harm and sends immense pain to the patient. This pain may be so immense, that the patient may become immobile.

The increased pressure on the scrotum may be caused by the combination of gravity and the weight of the fluid that has filled the edematous scrotum. This pressure must be redistributed in order for the fluid to be redistributed back to the body and away from the scrotum.

A popular method of redistributing the pressure is by repositioning and elevating the scrotum. This can be accomplished by simply turning or repositioning the entire body of the patient. Undesirably, this solution is not feasible for patients whose entire bodies cannot be repositioned due to medical conditions or illnesses.

For patients whose entire bodies cannot be repositioned, nurses may position rolled-up washcloths around the scrotum to try to elevate the scrotum. While this approach may have some degree of success, it also has several drawbacks. For instance, it is not exact and may not elevate the scrotum to the necessary position and does not provide adequate pressure redistribution. In addition, this method lacks consistency. For example, if the rolled-up washcloths were to be removed from the patient, it would be difficult to reposition them into their exact original configuration.

There is a continuing need for a scrotal edema support and method that repositions, elevates, and provides adequate pressure redistribution for the scrotum. Desirably, the scrotal edema support and method facilitate consistent placement.

SUMMARY

In concordance with the instant disclosure, a scrotal edema support and method that repositions, elevates, and provides adequate pressure redistribution for the scrotum, and which facilitates consistent placement, has been surprisingly discovered.

In one embodiment, a scrotal edema support has a main body with a top surface, a bottom surface, a first side, a second side, a rear end, and a front end. The top surface includes a flexing area and a resting area. The flexing area is disposed adjacent to the rear end of the main body. The resting area is disposed adjacent to the front end of the main body. The flexing area is configured to receive an edematous scrotum of a patient. The bottom surface has a sloped portion and a leveled portion. The sloped portion is disposed adjacent to the rear end of the main body. The leveled portion is disposed from the front end to the sloped portion. The sloped portion of the bottom surface is oriented at an angle relative to the leveled portion of the bottom surface.

In another embodiment, a system for scrotal edema support has a scrotal edema support and a fecal management system. The scrotal edema support includes a main body with a top surface, a bottom surface, a first side, a second side, a rear end, and a front end. The top surface includes a flexing area and a resting area. The flexing area is disposed adjacent to the rear end of the main body. The resting area is disposed adjacent to the front end of the main body. The flexing area is configured to receive an edematous scrotum of a patient. The bottom surface has a sloped portion and a leveled portion. The sloped portion is disposed adjacent to the rear end of the main body. The leveled portion is disposed from the front end to the sloped portion. The sloped portion of the bottom surface is oriented at an angle relative to the leveled portion of the bottom surface. The bottom surface further includes a channel formed therein. The fecal management system includes a catheter and a waste storage container. The catheter is configured to be in communication with a rectum of a patient and the waste storage container. The catheter is further being disposed adjacent to the channel of the scrotal edema support.

In yet another embodiment, a method for supporting an edematous scrotum of a patient includes the steps of providing a scrotal edema support. The scrotal edema support has a main body with a top surface, a bottom surface, a first side, a second side, a rear end, and a front end. The top surface includes a flexing area and a resting area. The flexing area is disposed adjacent to the rear end of the main body. The resting area is disposed adjacent to the front end of the main body. The flexing area is configured to receive an edematous scrotum of a patient. The bottom surface has a sloped portion and a leveled portion. The sloped portion is disposed adjacent to the rear end of the main body. The leveled portion is disposed from the front end to the sloped portion. The sloped portion of the bottom surface is oriented at an angle relative to the leveled portion of the bottom surface. Next, the edematous scrotum is disposed on the flexing area of the top surface of the scrotal edema support. Disposing the edematous scrotum on the flexing area further causes the rear end of the scrotal edema support to be moved downwardly at an angle of deflection. This orientates the scrotal edema support to facilitate the drainage of the edematous scrotum.

In exemplary embodiments, it is appreciated that the scrotum in a human is meant to protect the testicles that may produce viable sperm for reproduction. In the medical field, many times when a scrotum fills with fluid this is charted as "scrotal swelling" or "scrotal edema." With a sensation from the nervous system that a scrotum is fluid filled it is sending a message of severe pain. With this, is the issue that a patient almost becomes totally immobile due to an intense pain of the swollen scrotum. Gravity plays a large part in the pain of the scrotum in regard to where it is placed on the male anatomy. A fluid filled scrotum can develop into an array of medical conditions which could include hydrocele forms in the scrotum and in one of the testes, and with this diagnosis one of the testes has become twisted thus causing lack of blood flow into the scrotum to keep it healthy. This condition, if left untreated can lead to tissue death from lack of blood flow and swelling. Varicocele can cause infertility in the male. There are many other medical symptoms and diagnosis that causes a painful swollen scrotum, just a few may be cancer, kidney failure, heart failure, and hernias and during a surgical procedure.

Gravity along with a fluid filled scrotum places weight on the scrotum. It is documented when the scrotum becomes swollen it is very painful. The weight of the fluid filled scrotum can be immense and needs to be elevated to allow the fluid to dissipate back into the body. In helping patients to elevate and provide pressure redistribution in a scrotal device it can be rendered that the swelling will be reduced and can be utilized in helping to provide pain management for scrotal edema.

The wall of the scrotum is comprised of numerous layers, as follows.

1) The skin of the scrotum is very thin, pigmented and wrinkled. The skin forms a single pouch around the entire surface and diameter. In the very middle of the scrotum is a slightly raised ridge, this indicates the fusion of the two lateral labioscrotal swellings.

2) The superficial fascia is the second layer of the scrotum and is continuous with the fatty and membranous layers of fascia of the anterior abdominal wall. A fatty layer in this region is replaced by a very smooth muscle known as the dartos muscle. This muscle is innervated by sympathetic nerve fibers. The primary job of this muscle is responsible for the wrinkling of the skin on the scrotum. The membranous layer of the fascia in the scrotal region is known as Colle's fascia. It is continuous in front with the Scarpa's fascia (membranous layer of fascia of anterior abdominal wall). Both layers of the superficial fascia contribute to the median partition, which crosses the scrotum and separates the testes from each other.

3) The spermatic fascia lies beneath the superficial fascia and are derived from the three layers of anterior abdominal wall. These are comprised of: external spermatic fascia, derived from aponeurosis of the external oblique muscle.

4) Cremaster fascia is derived from the internal oblique muscle, this fascia is comprised of both the connective tissue and muscle fibers, which form and create the cremaster muscle.

5) The fifth layer of the scrotum is the internal spermatic fascia; it is derived from the fascia transversalis. The blood supply of the artery thus the venous blood drains through the testicular veins into the inferior vena cave which is very thin tissue.

The nerve supply to the scrotum is rather abundant, the scrotum has 1) Anterior and Posterior nerves 2) Genital branch of genitofemoral nerve (this nerve supplies the cremaster muscle) 3) the last nerve to supply the scrotal region is the perineal branches of the posterior femoral cutaneous nerves the scrotum receives its blood supply from the anterior scrotal artery (a branch of the deep external pudendal artery) and the posterior scrotal artery (a branch of the internal pudendal).

The cremaster muscle has a role in controlling the temperature. It can shrink the scrotum to move the testes near the abdomen or it can dilate the scrotum to move the testes away from abdomen. Temperature will rise when scrotum is near the abdomen and it will drop in the other case.

Another function the scrotum has is the lymph drainage system. Lymph from the skin, fasciae of the scrotum drains into the superficial inguinal lymph nodes. It is imperative to keep in mind that the lymph from the testes and the epididymis (structures contained within the scrotum) drains into the para-aortic lymph nodes at the level of first lumbar vertebra. This is because during development, testes migrate from high up on the posterior abdominal wall.

The primary function of scrotum is to provide a cooler environment to the testes. For spermatogenesis to occur, the testes must be present at a temperature slightly lower than the rest of the body.

When swelling occurs the nervous system perceives sensations that present a risk of harm and pain to the scrotum.

Pressure redistribution and elevation is a medical necessity to prevent scrotal edema and scrotal tissue breakdown. Although regular repositioning is mandated by the NPUAP (National Pressure Ulcer Advisory Panel and the AHRQ (American Healthcare Research and Quality) Guidelines in an acute care and long-term care, or home care setting it is sometimes hard to reposition a patient with terminal cancer, comatose patients, any one that is critically ill, paralyzed or medically compromised.

The disclosure of this application therefore includes a support device that can assist and support the appropriate positioning, weight distribution, and elevation of a fluid filled scrotum in the male anatomy while sitting or lying. This will also help to stabilize the scrotum while positioning. Such a device would have utility in a clinical application. This device would provide pressure redistribution and elevation to encourage hydraulic flow of fluids from the swollen scrotal area and to help allow the fluid to follow its natural process and dissipate from the scrotal area and be redistributed back into the body. In addition to a device helping to elevate and alleviate edema it would also be intended for pressure redistribution and to reduce the risk of pressure ulcer injuries and or tissue tears to the scrotum. One end of such a device would be tapered to fit closely to the buttocks area to allow a comfortable fit and to begin the hydraulic flow of fluid while still providing elevation, and pressure redistribution. This device would have a through cut channel on the underneath side to allow for the placement of the fecal management system tubing. This channel would be cut into the device at the time of manufacturing to allow the fecal management system tubing to remain in place whilst the device was being used and helping to assure that the tubing will not becoming dislodged from the patient.

This device would be of a soft material that would be used while lying or sitting. This pressure redistribution device would be useful to the clinical professionals, doctors, nurses, aides, and home care givers and family members taking care of loved ones. It is important to note that all licensed healthcare officials must follow the NPUAP (National Pressure Ulcer Advisory Panel) and the AHRQ Guidelines (America Healthcare Research and Quality) in regard to pressure ulcer injury protocol and guidelines while in their care.

When a patient is compromised with testicular swelling it is very painful, several different causes some which constitute medical emergency. Testicle torsion is a true medical emergency with interruption of blood flow and blood supply to the testicles and scrotum this can lead to tissue death of the affected testicle. Inflammation of the testicle (orchitis) or epididymis due to any cause can also lead to testicular swelling. A hydrocele is a benign buildup of fluid around a testicle that can appear as a testicular or scrotal swelling, other causes include anatomical abnormalities, infections, hernias, and tumors. A hydrocele is a benign buildup of fluid around a testicle that can appear as testicular or scrotal swelling. Congestive heart failure causes fluid buildup in the lower extremities; it can be so severe as to cause scrotal swelling.

Turning a patient or off-loading a pressure point in a swollen scrotum seems simplistic in concept but can be problematic when a patient is critically ill and or cannot be turned or re-positioned because of a medical condition and pain. Nursing care often uses rolled up washcloths to "try to elevate only" in and around the swollen scrotum to maintain desired positioning for comfort and to try to elevate the scrotum to dissipate the fluid, while this approach has some utility and some degree of success and while they are doing their best they are not always successful as these washcloths are purchased in bulk for institutional use and the institutional budget which often times allows only for rough and very thin poor quality washcloths.

The disclosure of this application as in the scrotal support would be to provide proper cushioning for pressure redistribution, support, elevation and tapered elevation to reduce the edema and help accelerate the lymphatic drainage process. This scrotal device would help with dissipating the engorged scrotal fluid back into the body, allow pressure redistribution, and has a channel to address the fecal management system tubing should that be in place in the critically ill patient.

The device of the disclosure is composed of a molecular makeup of such as polyurethane foam, cushioning material, gel, or air. In all cases the foam may be generally cut to a suitable size for its intended application of the male anatomy and body weight. For example, a foam block would be cut in a suitable manner such as by the use of a foam hot wire cutting machine or a cutting knife. The therapeutic device is intended to be used either in a lying down or a sitting position. The device would then be cut with the correct density of foam, cushioning material, gel or air which would be appropriate for the patient anatomy.

Further areas of applicability will become apparent from the description provided herein. It should be understood that the description and specific examples are intended for purposes of illustration only and are not intended to limit the scope of the present disclosure.

DRAWINGS

The above, as well as other advantages of the present disclosure, will become readily apparent to those skilled in the art from the following detailed description, particularly when considered in the light of the drawings described herein.

DETAILED DESCRIPTION

The following detailed description and appended drawings describe and illustrate various embodiments of the invention. The description and drawings serve to enable one skilled in the art to make and use the invention and are not intended to limit the scope of the invention in any manner. In respect of the methods disclosed, the order of the steps presented is exemplary in nature, and thus, is not necessary or critical unless otherwise disclosed.

Figure 9:
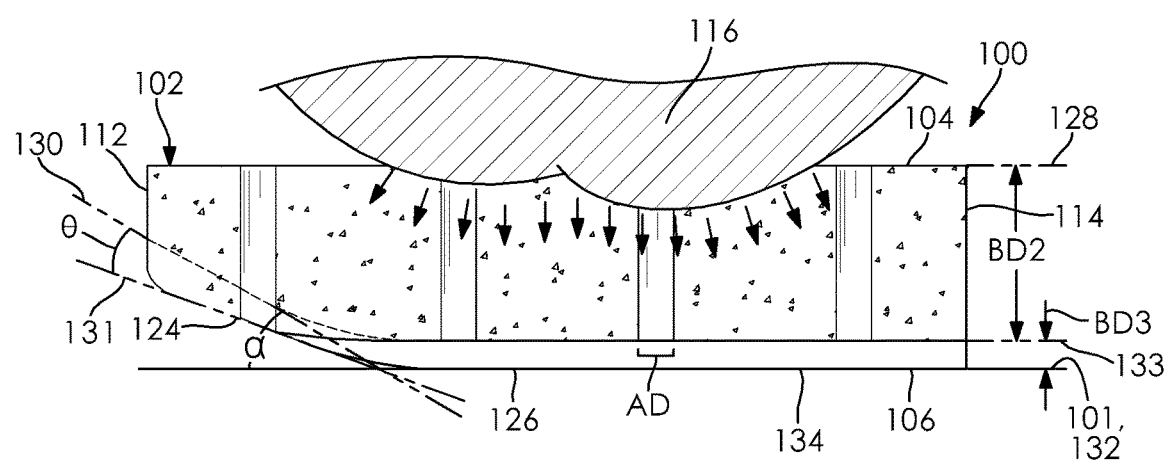
FIG. 9 is a cross-sectional side elevational view of the scrotal edema support taken a section line A-A in FIG. 8.
Figure 10:
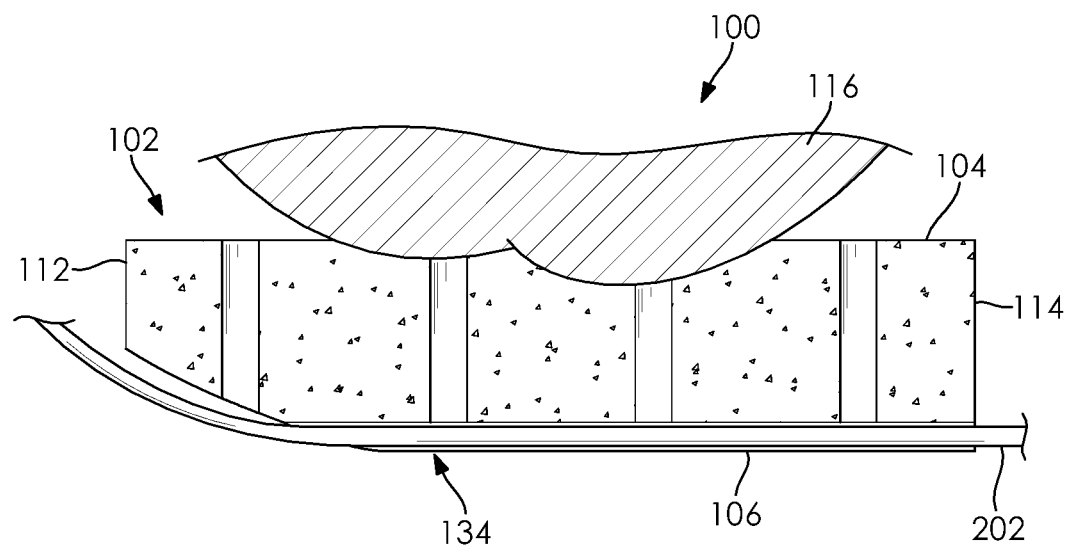
FIG. 10 is a cross-sectional side elevational view of the scrotal edema support taken at section line A-A in FIG. 8, and further showing a catheter of the fecal management system disposed in a channel of the scrotal edema support.
Figure 11:
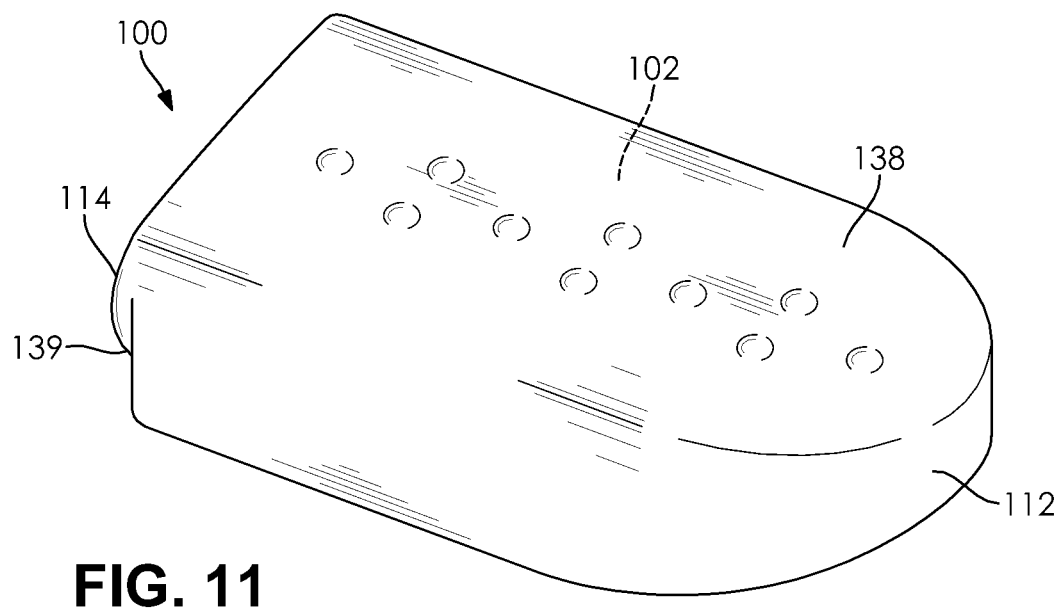
FIG. 11 is a top perspective view of the scrotal edema support shown in FIG. 1 disposed in a cover.

As shown in FIGS. 1-10, a scrotal edema support 100 has a main body 102. The main body 102 includes a top surface 104, a bottom surface 106, a first side 108, a second side 110, a rear end 112, and a front end 114. Although the support 100 is shown throughout FIGS. 1-10 without an outer covering, for purposes of illustrative in the structure of the support 100, it should be appreciated that the support 100 may be preferably used with the outer covering, for example, as shown in FIG. 11, in operation.

The main body 102 is configured to be a support and a cushioning material for an edematous scrotum 116 of a patient 118. In some embodiments, the main body 102 is manufactured from a soft and conformable cushioning material.

In particular embodiments, the main body 102 is manufactured from foam, such as polyurethane foam. Desirably, manufacturing the main body 102 from foam facilitates a support that is sturdy enough and has a sufficient density to elevate the edematous scrotum 116, while remaining soft enough to ease the pain of the patient 118. In certain examples, the foam may be selected to have a variable density along at least one of a length, a depth, and a width of the main body 102. It should be appreciated that a skilled artisan may manufacture the main body 102 from other suitable materials and densities within the scope of this disclosure.

In more specific embodiments, the main body 102 has a body length BL (shown in FIG. 6) of about nine and one-half inches (9.5"), a body width BW (shown in FIG. 6) of about four and one-half inches (4.5") and a body depth BD (shown in FIG. 3) of about two and one-half inches (2.5"). It should be appreciated that a person skilled in the art may select other suitable dimensions, as desired.

Figure 1:
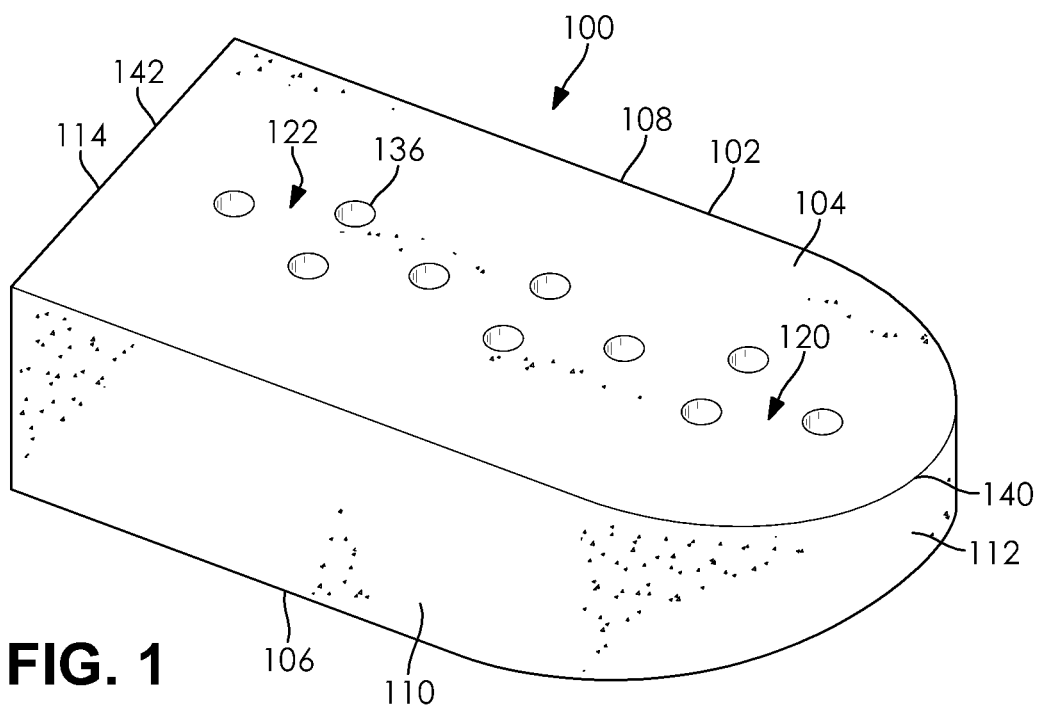
FIG. 1 is a top perspective view of a scrotal edema support according to one embodiment of the disclosure, and further showing a top surface of the scrotal edema support.
Figure 6:
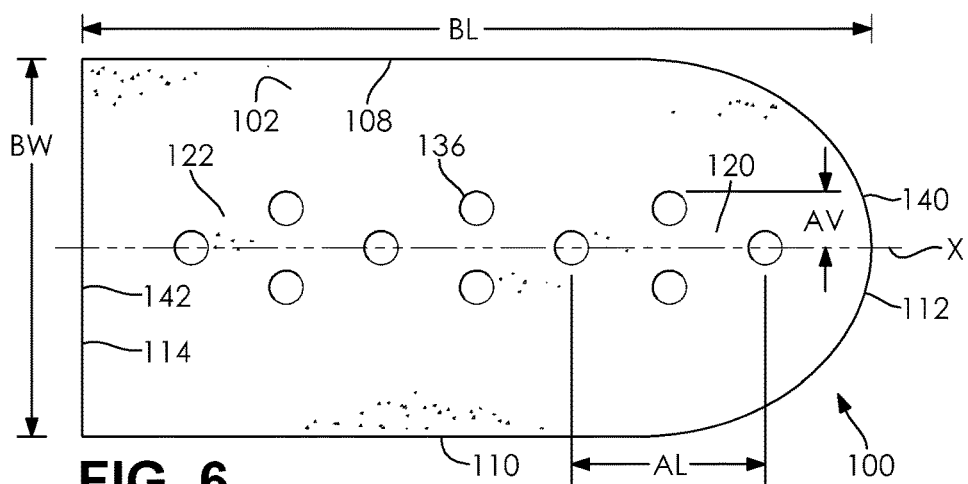
FIG. 6 is a top plan view of the scrotal edema support shown in FIG. 1, and further showing a flexing area and a resting area.

Now referencing FIGS. 1 and 6, the top surface 104 has a flexing area 120 and a resting area 122. At least one of the flexing area 120 and the resting area 122 is configured to receive the edematous scrotum 116 of the patient 118. The rear end 112 including the flexing area 120 is configured to be placed in the peritoneum region of the patient. In certain examples, where the edematous scrotum 116 is sufficiently large, both the flexing area 120 and the resting area 122 may simultaneously receive and support the edematous scrotum 116 of the patient 118.

Figure 8:
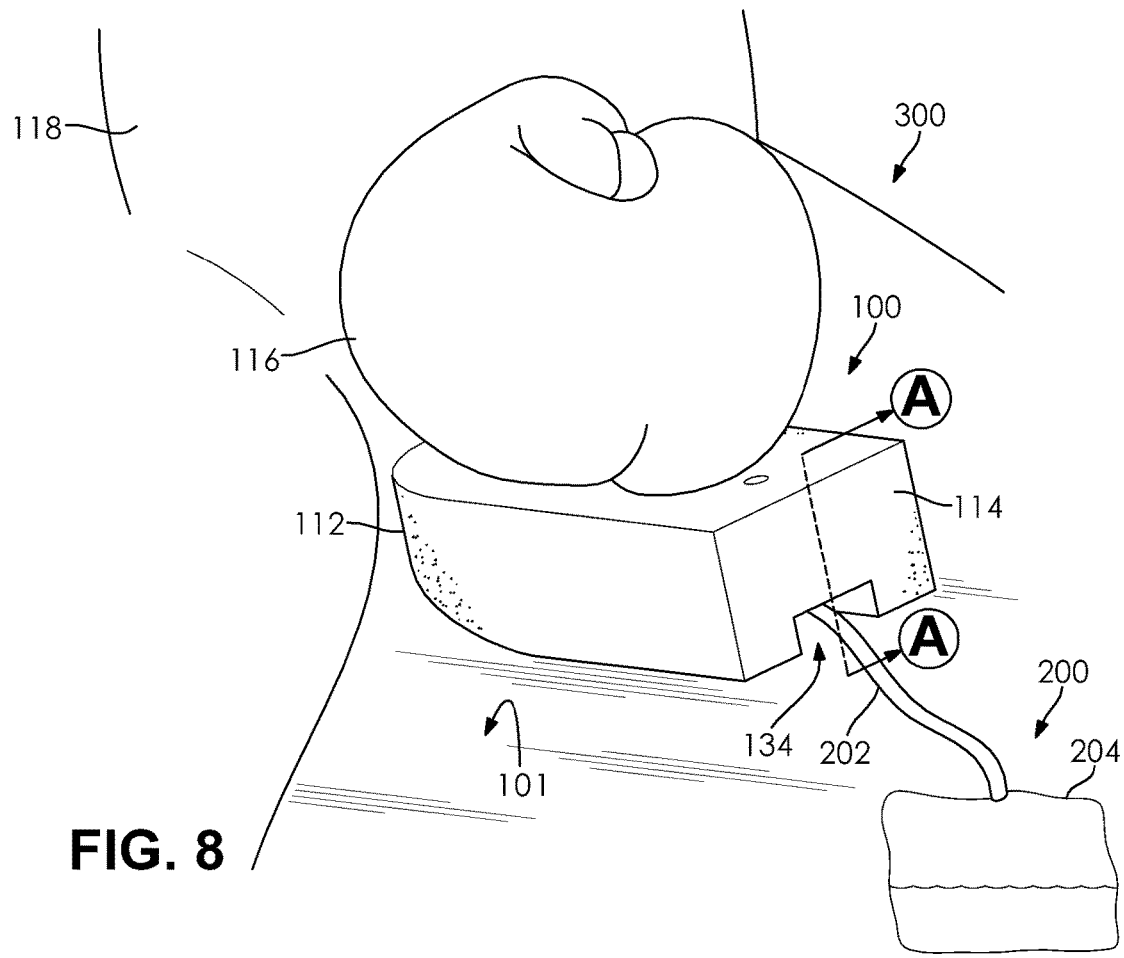
FIG. 8 is top perspective view of a system for scrotal edema support, further showing the scrotal edema support shown in FIG. 1 and a fecal management system in use.

The flexing area 120 is disposed adjacent to the rear end 112 of the main body 102. As shown in FIGS. 8-10, and will be described in further detail below, where the edematous scrotum 116 is disposed on the flexing area 120, the rear end 112 is caused to be pushed, moved, or compressed downwardly at an angle of deflection θ. Desirably, this orients the edematous scrotum 116 at such a deflection angle θ that facilitates the drainage of the edematous scrotum 116.

The resting area 122 is disposed adjacent to the front end 114 of the main body 102, as shown in FIGS. 1 and 6. As mentioned above, and in further detail below, the front end 114 of the main body 102 is also pressed against a surface 101 underlying the patient where the flexing area 120 of the top surface 104 receives the edematous scrotum 116 of the patient 118.

Figure 2:
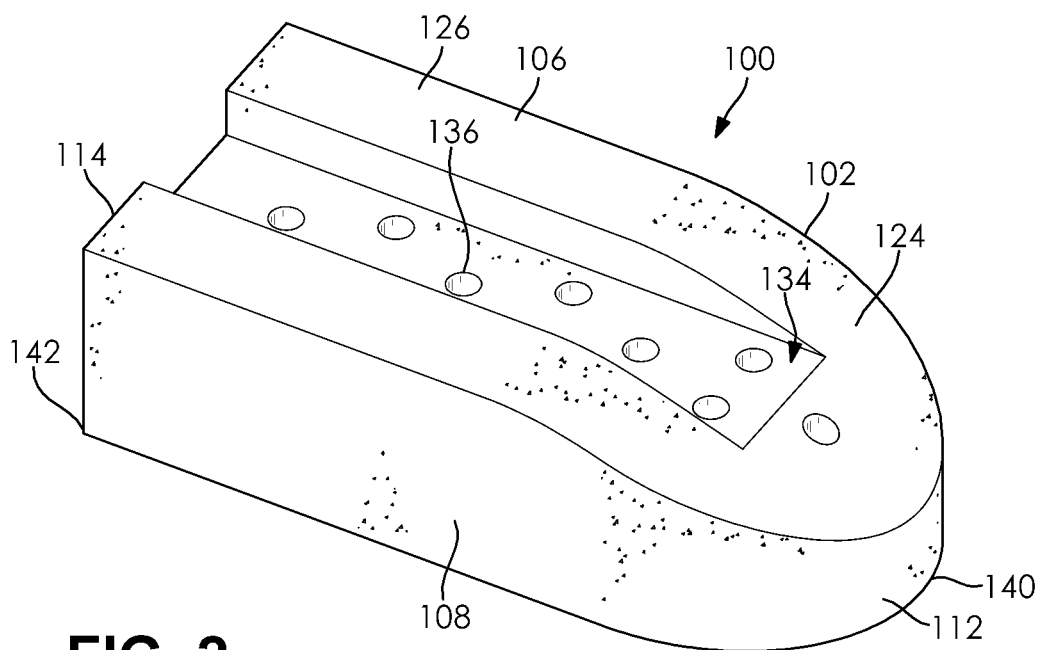
FIG. 2 is a bottom perspective view of the scrotal edema support shown in FIG. 1, and further showing a bottom surface of the scrotal edema support.
Figure 7:
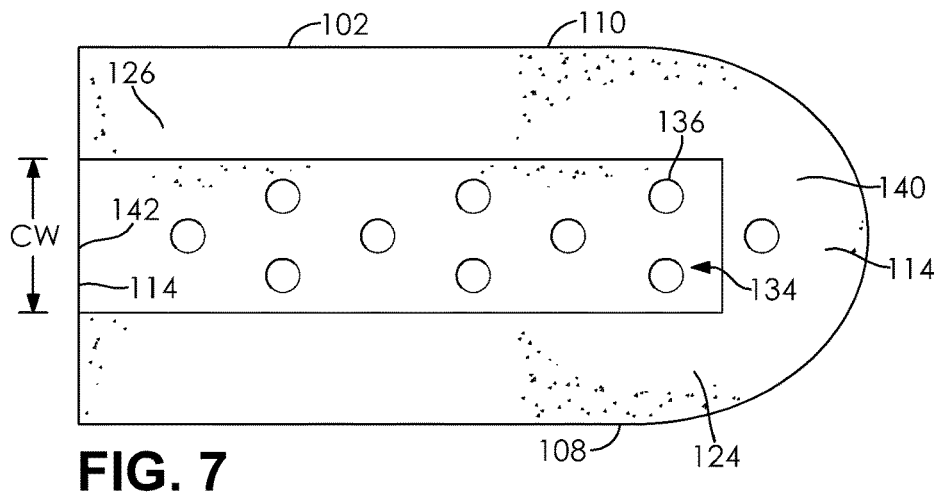
FIG. 7 is a bottom plan view of the scrotal edema support showing in FIG. 1, and further showing a leveled portion and a sloped portion.

With reference to FIGS. 2 and 7, the bottom surface 106 of the main body 102 includes a sloped portion 124 and a leveled portion 126. The sloped portion 124 is disposed adjacent to the rear end 112 of the main body 102. The leveled portion 126 is disposed from the front end 114 of the main body 102 to the sloped portion 124. In addition, the sloped portion 124 of the bottom surface 106 is oriented at an angle relative to the leveled portion 126 of the bottom surface 106, as described further hereinbelow. Advantageously, the angle of the sloped portion 124 permits the rear end 112 to be depressed or pushed downwardly by a further angle of deflection θ (shown in FIG. 9) where the edematous 116 is disposed on the flexing area 120, as shown in FIGS. 8-10.

In some embodiments, and as shown in FIG. 9, the top surface 104 of the main body 102 is disposed on a first plane 128, the sloped portion 124 of the bottom surface 106 is disposed on a second plane 130, 131 (with the second plane 130 being in an unused state and the second plane 131 being in a used state), and the leveled portion 126 of the bottom surface 106 (configured to rest upon the surface 101 such as a bed or seat) is disposed on a third plane 132. The third plane 132 may be defined by a resting surface 101 on which the support 100 is disposed, for example, as shown in FIG. 9. The first plane 128 may be oriented parallel to the third plane 132. The second plane 130 is oriented transverse to the third plane 132, and thereby defines an angle α (shown in FIG. 9) of the sloped portion 124.

In particular examples, the angle α of the sloped portion 124 defined by the second plane 130 and the third plane 132 is between about one degree (1°) and ninety degrees (90°). In more particular examples, the angle α is between about seven degrees (7°) and about twenty-four degrees (24°). In most particular examples, the angle α is about seventeen degrees (17°). It should be appreciated that a skilled artisan may select different degrees of angle α for the sloped portion 124 of the bottom 106 of the main body 102, in order to accommodate different sizes and types of edematous scrotum 116, as desired.

Figure 3:
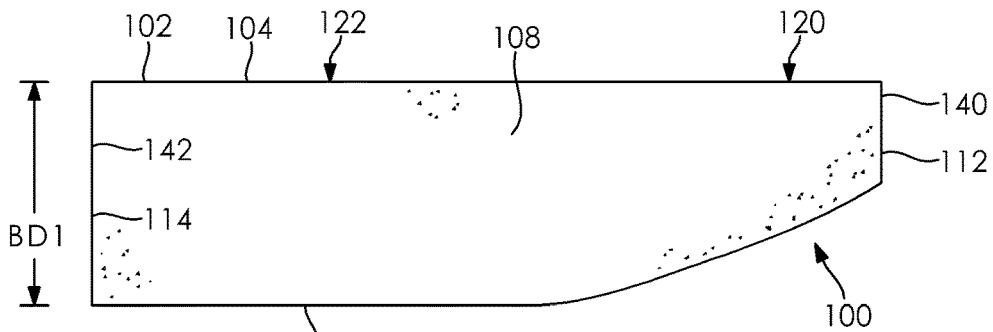
FIG. 3 is right side elevational view of the scrotal edema support shown in FIG. 1, and further showing a first side of the scrotal edema support.
Figure 4:
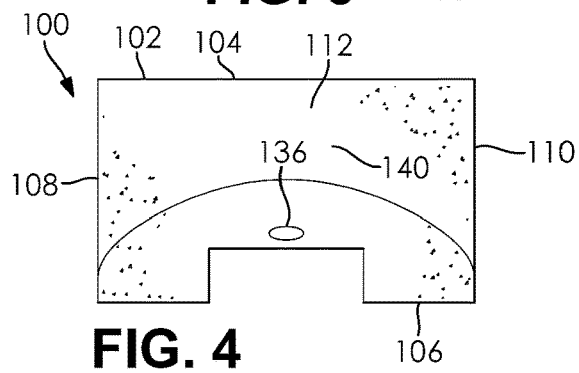
FIG. 4 is a front elevational view of the scrotal edema support shown in FIG. 1, and further showing a front end of the scrotal edema support.

In addition, it should be appreciated that the angle of deflection θ described further hereinabove may be defined by the angle between the second plane 130 in the unused state, for example, as shown in FIG. 3, and the second plane 131 in the used state, for example, as shown in FIG. 9. In other words, the angle of deflection θ is a change in the angle α associated with the sloped portion 124 of the bottom 106 of the main body 102 where the support 100 is being used.

Now referencing FIGS. 2 and 7, the bottom surface 106 of the main body 102 may further includes a channel 134 formed therein. The channel 134 is configured to receive a fecal management system 200 (shown in FIGS. 8 and 10), and which will be discussed in more detail below. In particular examples, the channel 134 extends from the front end 114 of the main body 102 to the second plane 130. The channel 134 provides a space for the fecal management system 200 to be received. Advantageously, this militates against the fecal management system 200 from being inadvertently crushed or closed by the patient 118 where the edematous scrotum 116 is disposed on the flexing area 120.

In specific embodiments, and as shown in FIG. 9, an upper surface of the channel 134 is disposed on a fourth plane 133. The fourth plane 133 is oriented parallel to the first plane 128. In addition, the main body 102 of the scrotal edema support 100 may have a first body depth BD1 (shown in FIG. 3), a second body depth BD2 (shown in FIG. 9) and a third body depth BD3 (shown in FIG. 9). The first body depth BD1 is defined by the distance the first plane 128 and the third plane 138. The second body depth BD2 is defined by the distance between the first plane 128 and the fourth plane 133. The third body depth BD3 is defined by the distance between the fourth plane 133 and the third plane 132, and likewise defines a depth of the channel 134 of the main body 102.

Figure 5:
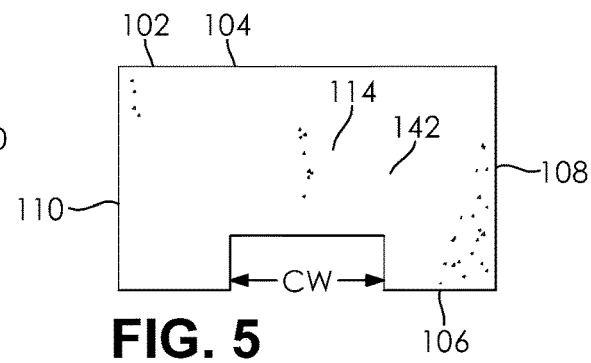
FIG. 5 is a rear elevational view of the scrotal edema support shown in FIG. 1, and further showing a rear end of the scrotal edema support.

In certain embodiments, the first depth BD1 may be about two and one-half inches (2.5"), and the second depth BD2 is about one and three-fourths inches (1.75") and the third depth BD3 is about three-fourths of an inch (0.75"). In addition, the channel 134 may have a channel width CW (shown in FIG. 5) of about two inches (2"), as shown in FIGS. 5 and 7. Although these dimensions have been shown to be useful, other dimensions may be selected by one skilled in the art, as desired.

In further embodiments, the main body 102 may further include a plurality of apertures 136, as shown in FIGS. 1, 4, and 6-7. The plurality of apertures 136 are configured to facilitate a compressibility of the top surface 104 in operation. It is also believed that this allows for better pressure redistribution. Desirably, this better pressure redistribution results in less pain for the patient 118. It should be appreciated that a person skilled in the art may select any number of the plurality of apertures 136 within the scope of this disclosure.

In some examples, the plurality of apertures 136 are formed through the main body 102 from the top surface 104 to the channel 134 formed in the bottom surface 106. In other examples, at least a portion of the plurality of apertures 136 is formed through the main body 102 from the top surface 104 to the channel 134 formed in the bottom surface 106. In particular examples the plurality of apertures 136 is in an alternating "1-2" pattern, as shown in FIGS. 1 and 6. In this patter, a first row of the apertures 136 may be arranged along a bisecting longitudinal axis X of the main body 102, and adjacent second rows of the aperture 136 may be spaced apart from the longitudinal axis X a distance AV. Likewise, the apertures 136 may be spaced apart from each other in their individual rows a distance AL. In a particular example, the distance AL may be about four times the distances AL. It is believed that this configuration of the plurality of apertures 136 facilitates better pressure redistribution. Nonetheless, a skilled artisan may employ different configurations of the plurality of apertures 136, having other suitable distributions of the apertures including different distances AV and AL, as desired.

In specific embodiments, each of the plurality of apertures 136 has an aperture diameter AD of about one-half inch (0.5"), as shown in FIG. 9. It is believed that this facilitates better pressure redistribution in practice. It should also be appreciated that although the diameter AD has been shown to be useful, the diameter AD is scalable by a person skilled in the art, as desired.

Now referencing FIG. 11, the scrotal edema support 100 may further include a cover 138. The cover 138 is configured to be removably disposed over the main body 102, with the main body 102 being removable through an opening 139 formed in one end of the cover 138. Desirably, having the cover 138 be removeable, permits the cover 138 to be washed between uses or even replaced. This militates against the spread of infections and bacteria between different patients 118. In addition, the cover 138 may be manufactured from moisture wicking fabrics. Advantageously, moisture wicking fabrics aid in wicking excess moisture from the edematous scrotum 116 of the patient 118. Non-limiting examples of moisture wicking fabrics include synthetic fibers, such as polyester or nylon. Other moisture wicking fabrics may be selected by a skilled artisan, as desired.

In further embodiments, the rear end 112 of the scrotal edema support 100 may include a curved edge 140, as shown in FIGS. 1-7. The curved edge 140 facilitates the insertion of the support 100 between the legs of the patient. In addition, the front end 114 may include a planar edge 142, also shown in FIGS. 1-7. It believed that both the curved edge 140 and the planar edge 142 facilitate better pressure redistribution. It should be appreciated that other shapes may be employed by a skilled artisan within the scope of this disclosure.

With reference to FIG. 8, a system for scrotal edema support 300 includes the scrotal edema support 100 and the fecal management system 200. The fecal management system 200 is configured to reroute biowaste from the patient 118 to the waste storage container 204 for collection and subsequent hygienic disposal.

In particular examples, the fecal management system 200 has a catheter 202 and a waste storage container 204. The catheter 202 is configured to be placed in communication with a rectum (not shown) of the patient 118 and the waste storage container 204. The catheter 202 is further configured to be disposed adjacent to the channel 134 of the scrotal edema support 100. Desirably, the channel 134 together with the sloped portion 124 of the bottom surface 106 of the main body 102 are configured to militate against the catheter 202 being crushed by the patient 118 in operation.

Figure 12:
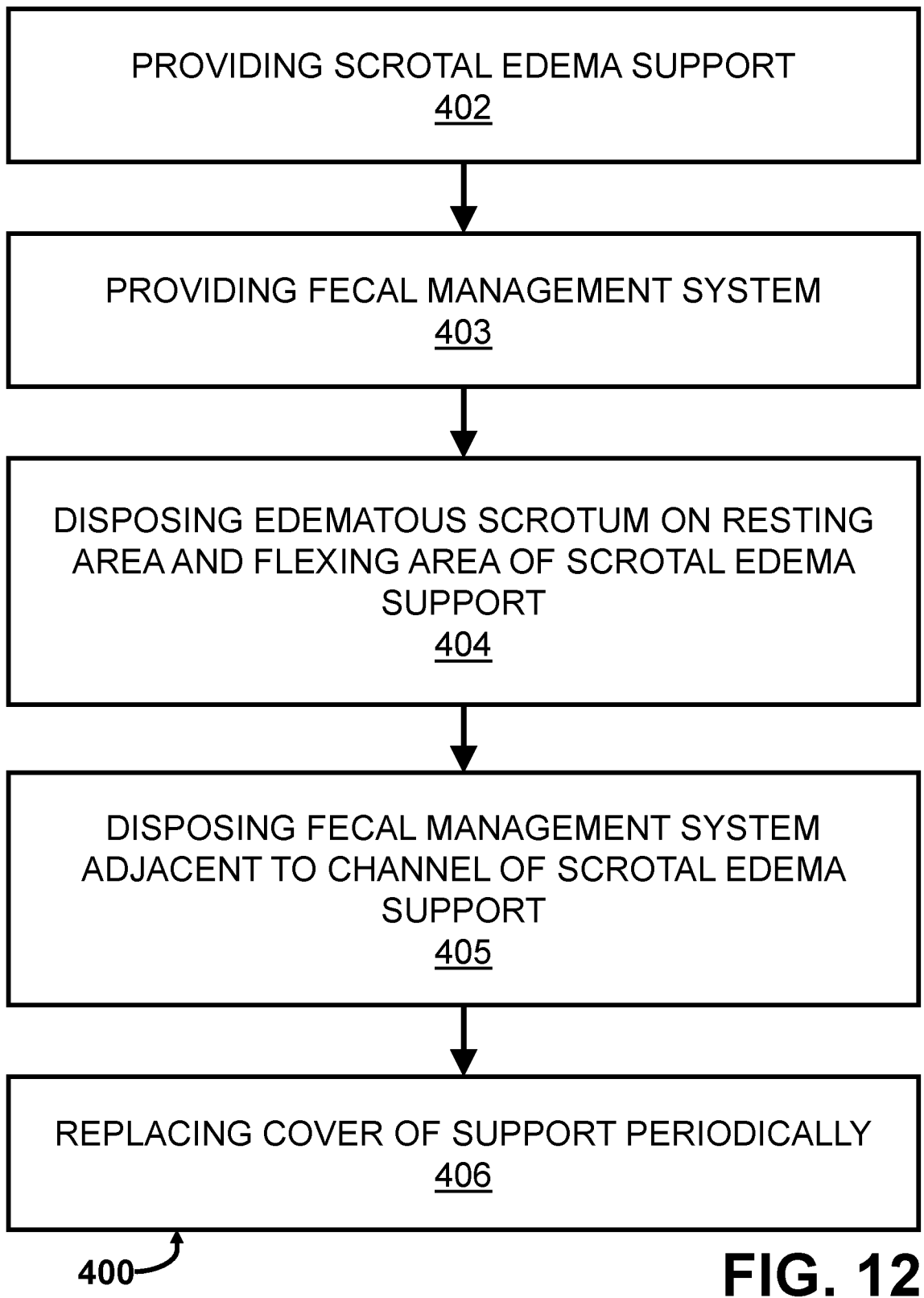
FIG. 12 is a flowchart illustrating a method for supporting an edematous scrotum of a patient according to one embodiment of the disclosure.

Referring now to FIG. 12, a method for supporting an edematous scrotum of a patient 400 is shown. The method 400 includes a step 402 of providing the scrotal edema support 100. Next, the edematous scrotum 116 of the patient 118 is disposed on at least one of the flexing area 120 and the resting area 122 of the top surface 104 of the scrotal edema support 100, in a step 404. Disposing the edematous scrotum 116 on the flexing area 120 causes the rear end 112 of the scrotal edema support 100 to be moved downwardly. As shown in FIGS. 8-10, moving the rear end 112 downwardly may thereby orient the sloped portion 124 of the scrotal edema support 100 at a slightly downward angle θ relative to the surface 101.

Desirably, this also orients the edematous scrotum 116 in such a way to facilitate the drainage of the edematous scrotum 116. It should be appreciated that the drainage of the edematous scrotum 116 is directly related to the deflection angle θ. For example, having a larger deflection angle θ may permit increased drainage of the edematous scrotum 116. Likewise, having a smaller deflection angle θ may permit less drainage of the edematous scrotum 116. Therefore, a person skilled in the art may scale the deflection angle θ by selecting other angles to the sloped portion 124 or densities and types of the foam material for the main body 102 to accommodate different sizes and types of the edematous scrotum 116.

In addition, and advantageously, the scrotal edema support 100 is always oriented in the same orientation via the angle of deflection θ. Therefore, medical personal may be able to elevate the edematous scrotum 116 in a consistent orientation via the scrotal edema support 100. By moving the main body 102 relative to the edematous scrotum 116, different angles of deflection θ may also be selected by medical personnel within the scope of the disclosure, as desired.

In some embodiments, the method 400 includes a step of placing the scrotal edema support 100 within the cover 138. The method 400 then further includes a step 406 of replacing the cover 138 periodically or on a predetermined regular basis. Desirably, replacing the cover 138 with a new cover 138 or a cover 138 that's been cleaned or sanitized, militates against the spread of infections and bacteria to and from the patient 118. It should be appreciated that periodic interval of replacing the cover 138 is scalable by a skilled artisan, according to the needs of the patient 118 and healthcare guidelines.

In further embodiments, the method 400 includes the step 403 of providing the fecal management system 200. The method 400 then further includes a step 405 of disposed the catheter 202 of the fecal management system 200 adjacent to the channel 134 of the scrotal edema support 100, for example inside of the channel 134 along the length of the main body 102. Advantageously, the channel 134 provides a covering for the catheter 202 to militate against it from being crushed by the patient 118 while in operation.

EXAMPLES

The device 100 was proven in the medical field to have a utility by making and testing several prototypes.

Example 1. The scrotal device 100 that encompasses the features of the disclosure was prepared by first cutting a sheet of polyurethane foam 8"×10"×54" on a cutting table with a hot wire saw blade. Then, it was then placed on the convoluting machine for a shallow peak and valley convolution. Next, the 8"×10"×54" piece of convoluted foam is then run through a CNC machine and is digitally programmed to cut the peaks and valleys off the piece of foam. Subsequently, the 2.5"×4.5"×10" is placed on the CNC machine and programmed to cut to the desired shape of the scrotal device 2.5"×4.5"×9.5". Then, a desired shape of the scrotal support is then run through the CNC machine and the fecal management system channel is cut through the entire length of the underneath side of the scrotal device 100. Finally, the device 100 is then reinserted on the CNC programmable machine and is programmed to cut a taper on the rounded end of the scrotal device 100.

Example 2. Essentially the same device 100 was made as in Example 1 except that the density of foam in this example was higher than the first example. This created a device to support a larger, heavier edematous scrotum 116.

Advantageously, the scrotal edema support 100, the system for scrotal edema support 300, and the method for supporting an edematous scrotum of a patient 400 repositions and elevates the scrotum. In addition, the scrotal edema support 100 always orients the edematous scrotum 116 in the same orientation via the angle associated with the sloped portion 124, thereby facilitating consistent placement by medical personal. The subject device 100 is intended for use where therapeutic support, cushioning, tapered elevation and in controlling or reducing edema where lymphatic drainage is needed in the scrotal area of the male anatomy.

Furthermore, it should be appreciated that the pressure redistribution scrotal support device 100 of the present disclosure is unique in that it provides all the following criteria needed by the medical professional in providing good patient care following the guidelines of care according to the NPUAP and AHRQ guidelines addressing five key things relevant to good care of a patient with a swollen scrotum, namely—1) elevation, 2) tapered elevation, 3) pressure redistribution, 4) channeled underneath to accommodate the fecal management system, and 5) skin tears. This device 100 importantly stabilizes tissues that might be susceptible to discomfort or damage due to prolonged pressures on the tissues from undesired movement of the scrotum.

While certain representative embodiments and details have been shown for purposes of illustrating the invention, it will be apparent to those skilled in the art that various changes may be made without departing from the scope of the disclosure, which is further described in the following appended claims.

What is claimed is:

1. A scrotal edema support, comprising:
   a main body having a top surface, a bottom surface, a first side, a second side, a rear end, and a front end,
   the top surface having a flexing area and a resting area, the flexing area disposed adjacent to the rear end of the main body and the resting area disposed adjacent to the front end of the main body, and the flexing area configured to receive an edematous scrotum of a patient, and
   the bottom surface having a sloped portion and a leveled portion, the sloped portion disposed adjacent to the rear end of the main body and the leveled portion disposed from the front end to the sloped portion, the sloped portion of the bottom surface oriented at an angle relative to the leveled portion of the bottom surface,
   wherein the top surface is disposed on a first plane, the sloped portion of the bottom surface is disposed on a second plane, and the leveled portion is disposed on a third plane, and the second plane is oriented traverse to the third plane and defining an angle therebetween, the angle being between one degree (1°) and ninety degrees (90°).

2. The scrotal edema support of claim 1, wherein the bottom surface has a channel formed therein, the channel extending from the front end of the main body to the second plane on which the sloped portion of the bottom surface is disposed, and the channel configured to receive a fecal management system.

3. The scrotal edema support of claim 2, wherein the main body further has a plurality of apertures formed through the main body from the top surface to the bottom surface of the main body.

4. The scrotal edema support of claim 3, wherein at least a portion of the plurality of apertures are formed through the main body from the top surface to the channel formed in the bottom surface.

5. The scrotal edema support of claim 3, wherein each of the apertures has a diameter of about one-half inch (0.5").

6. The scrotal edema support of claim 2, wherein the fecal management system includes a catheter and a waste storage container.

7. The scrotal edema support of claim 6, wherein the catheter is configured to be in communication with both a rectum of the patient and the waste storage container.

8. The scrotal edema support of claim 1, wherein the angle is between about seven degrees (7°) and about twenty-four degrees (24°).

9. The scrotal edema support of claim 8, wherein the angle is about seventeen degrees (17°).

10. The scrotal edema support of claim 1, further comprising a cover removably disposed over the main body.

11. The scrotal edema support of claim 10, wherein the cover is a moisture wicking fabric including polyester.

12. The scrotal edema support of claim 1, wherein the first plane is oriented parallel to the third plane.

13. The scrotal edema support of claim 1, wherein the main body is a polyurethane foam.

14. The scrotal edema support of claim 1, wherein the rear end has a curved edge.

15. The scrotal edema support of claim 1, wherein the front end has a planar edge.

16. A method for supporting an edematous scrotum of a patient, comprising the steps of:
   providing a scrotal edema support including a main body having a top surface, a bottom surface, a first side, a second side, a rear end, and a front end, the top surface having a flexing area and a resting area, the flexing area disposed adjacent to the rear end of the main body and the resting area disposed adjacent to the front end of the main body, and the flexing area configured to receive an edematous scrotum of the patient, and the bottom surface having a sloped portion and a leveled portion, the sloped portion disposed adjacent to the rear end of the main body and the leveled portion disposed from the front end to the sloped portion, the sloped portion of the bottom surface oriented at an angle relative to the leveled portion of the bottom surface, wherein the top surface is disposed on a first plane, the sloped portion of the bottom surface is disposed on a second plane, and the leveled portion is disposed on a third plane, and the second plane is oriented traverse to the third plane and defining an angle therebetween, the angle being between one degree (1°) and ninety degrees (90°); and
   disposing the edematous scrotum on the flexing area of the top surface of the scrotal edema support, wherein the rear end of the scrotal edema support is caused to move downwardly, thereby orienting the scrotal edema support to facilitate drainage of the edematous scrotum.

17. The method of claim 16, wherein the scrotal edema support further includes a cover removably disposed over the main body, and the method further includes a step of replacing the cover periodically.

18. The method of claim 16, wherein the scrotal edema support has a channel formed in the bottom surface of the main body, and the method further includes the steps of:
   providing a fecal management system having a catheter and a waste storage container, the catheter configured to be in communication with a rectum of the patient and the waste storage container; and
   disposing the catheter of the fecal management system adjacent the channel of the scrotal edema support.

19. A system for scrotal edema support, comprising:
   a scrotal edema support including a main body having a top surface, a bottom surface, a first side, a second side, a rear end, and a front end, the top surface having a flexing area and a resting area, the flexing area disposed adjacent to the rear end of the main body and the resting area disposed adjacent to the front end of the main body, and the flexing area configured to receive an edematous scrotum of a patient, and the bottom surface having a sloped portion and a leveled portion, the sloped portion disposed adjacent to the rear end of the main body and the leveled portion disposed from the front end to the sloped portion, the sloped portion of the bottom surface oriented at an angle relative to the leveled portion of the bottom surface, wherein the bottom surface has a channel formed therein; and a fecal management system having a catheter and a waste storage container, the catheter configured to be in communication with a rectum of the patient and the waste storage container, and the catheter further being disposed adjacent the channel of the scrotal edema support.

\* \* \* \* \*